United States Patent
Li et al.

(10) Patent No.: US 11,054,351 B2
(45) Date of Patent: Jul. 6, 2021

(54) STRAIN AND ACOUSTIC WAVE TESTING DEVICE AND METHOD FOR HIGH-TEMPERATURE ROCK SAMPLE

(71) Applicant: SOUTHWEST PETROLEUM UNIVERSITY, Chengdu (CN)

(72) Inventors: Gao Li, Chengdu (CN); Ze Chen, Chengdu (CN); Yijian Chen, Chengdu (CN); Xin Yu, Chengdu (CN); Dong Liu, Chengdu (CN); Yi Zhang, Chengdu (CN)

(73) Assignee: SOUTHWEST PETROLEUM UNIVERSITY, Chengdu (CN)

( * ) Notice: Subject to any disclaimer, the term of this patent is extended or adjusted under 35 U.S.C. 154(b) by 391 days.

(21) Appl. No.: 16/305,943

(22) PCT Filed: Sep. 27, 2017

(86) PCT No.: PCT/CN2017/103762
§ 371 (c)(1),
(2) Date: Nov. 30, 2018

(87) PCT Pub. No.: WO2018/233120
PCT Pub. Date: Dec. 27, 2018

(65) Prior Publication Data
US 2020/0333221 A1    Oct. 22, 2020

(30) Foreign Application Priority Data

Jun. 23, 2017    (CN) .......................... 201710484758.0

(51) Int. Cl.
*G01N 3/08*    (2006.01)
*G01N 3/06*    (2006.01)
(Continued)

(52) U.S. Cl.
CPC ............... *G01N 3/08* (2013.01); *G01D 21/02* (2013.01); *G01N 3/06* (2013.01); *G01N 33/24* (2013.01);
(Continued)

(58) Field of Classification Search
CPC .. G01N 3/08; G01N 3/06; G01N 3/18; G01N 3/12; G01N 33/24; G01N 2203/0019;
(Continued)

(56) References Cited

U.S. PATENT DOCUMENTS

2016/0109603 A1* 4/2016 Jin .......................... E21B 49/02
                                                73/152.58

FOREIGN PATENT DOCUMENTS

CN    101614640 A    12/2009
CN    102967611 A    3/2013
(Continued)

*Primary Examiner* — Jonathan M Dunlap
(74) *Attorney, Agent, or Firm* — Bayramoglu Law Offices LLC

(57) ABSTRACT

A strain and acoustic wave testing device includes an acoustic wave transmitting terminal, an upper pressure-bearing shaft, corundum ejector pins, an upper displacement slide, a lower displacement slide, a heat insulation shell, a carbon fiber sleeve, a rock sample, a lower pressure-bearing shaft, an acoustic wave receiving terminal, a lower copper electrode, pearl powder, a temperature sensor, a transformer, a temperature-acoustic wave control box, an oscilloscope, an upper copper electrode, and a data collection and processing system.

1 Claim, 1 Drawing Sheet

(51) Int. Cl.
*G01N 33/24* (2006.01)
*G01D 21/02* (2006.01)
*G01N 3/12* (2006.01)
*G01N 29/04* (2006.01)
*G01N 3/18* (2006.01)

(52) U.S. Cl.
CPC ............... *G01N 3/12* (2013.01); *G01N 3/18* (2013.01); *G01N 29/04* (2013.01); *G01N 2203/0019* (2013.01); *G01N 2203/0226* (2013.01); *G01N 2203/0252* (2013.01); *G01N 2203/0256* (2013.01); *G01N 2203/0658* (2013.01)

(58) Field of Classification Search
CPC ... G01N 2203/0226; G01N 2203/0256; G01N 2203/0232; G01N 29/04; G01N 2203/0658; G01D 21/02
See application file for complete search history.

(56) References Cited

FOREIGN PATENT DOCUMENTS

| | | | |
|---|---|---|---|
| CN | 203083883 U | | 7/2013 |
| CN | 103901107 A | | 7/2014 |
| CN | 203785967 U | | 8/2014 |
| CN | 204302097 U | | 4/2015 |
| CN | 104865137 A | | 8/2015 |
| CN | 105092387 A | | 11/2015 |
| CN | 105510142 A | * | 4/2016 |
| CN | 105606454 A | * | 5/2016 |
| CN | 205643032 U | | 10/2016 |
| CN | 106525567 A | * | 3/2017 |
| CN | 106769511 A | * | 5/2017 |
| CN | 107101890 A | | 8/2017 |
| CN | 206920246 U | | 1/2018 |
| CN | 108240942 A | * | 7/2018 |
| JP | H0450636 A | | 2/1992 |

* cited by examiner

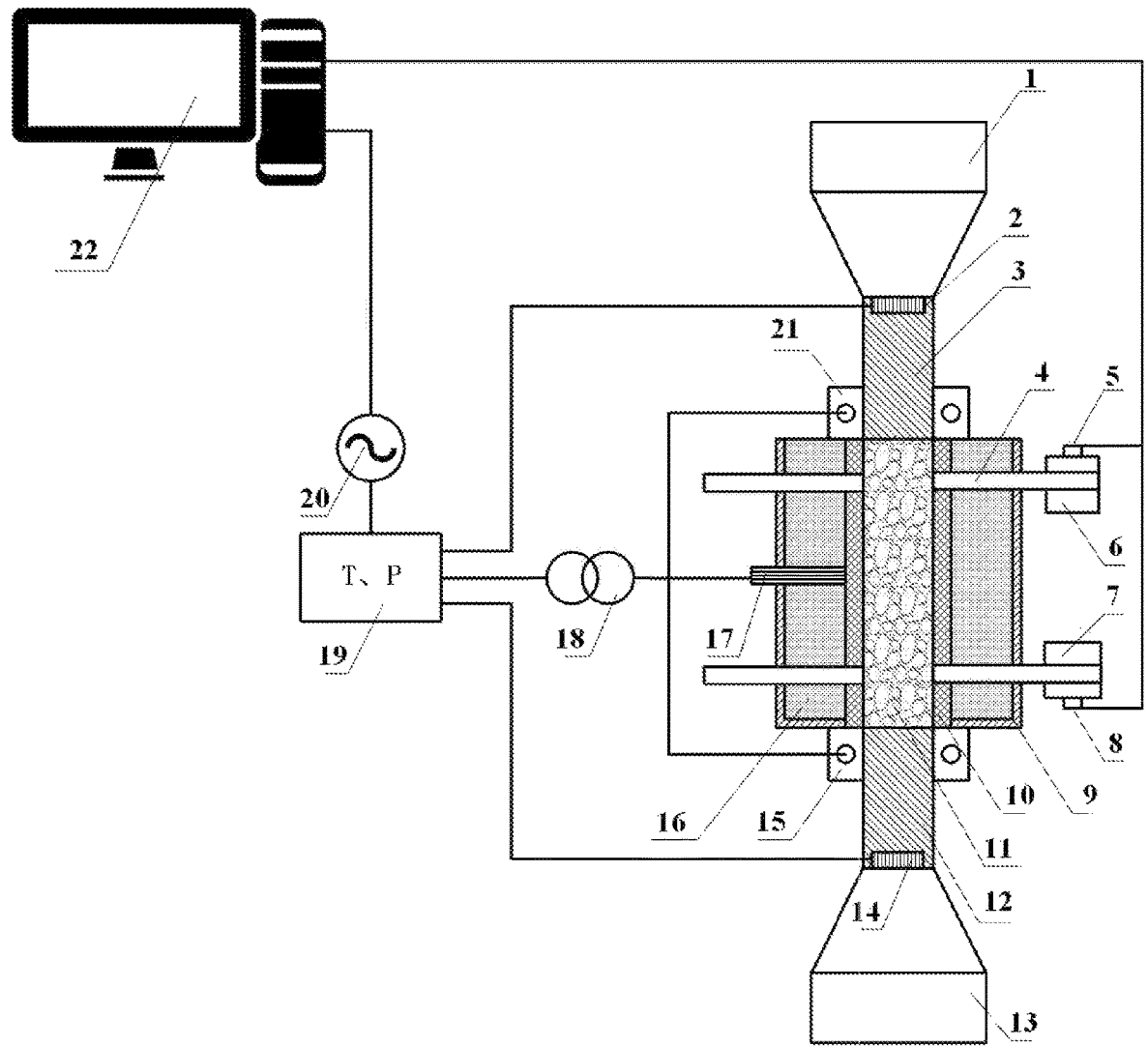

STRAIN AND ACOUSTIC WAVE TESTING DEVICE AND METHOD FOR HIGH-TEMPERATURE ROCK SAMPLE

CROSS REFERENCE TO THE RELATED APPLICATIONS

This application is the national phase entry of International Application No. PCT/CN2017/103762, filed on Sep. 27, 2017, which claims priority to Chinese Patent Application 201710484758.0 filed on Jun. 23, 2017, the entire contents of which are incorporated herein by reference.

TECHNICAL FIELD

The present invention relates to a strain and acoustic wave testing device and method for a high temperature rock sample of a uniaxial mechanical tester in the field of high temperature rock mass geothermal development and oil and gas well engineering.

BACKGROUND

Under high temperature conditions, due to the different thermal expansions of various mineral particles constituting rock, microcracks appear inside the rock, which leads to the deterioration of the mechanical properties of the rock and causes the wall of a geothermal development well or an oil and gas well to be unstable, resulting in serious security incidents, such as collapse. Therefore, the study on the variation law of the mechanical parameters of the rock is of a great practical significance under high temperature.

The Chinese patent CN205643032U discloses a uniaxial testing device for high-temperature stability of an asphalt mixture, which can simulate the process of temperature change from a road surface when an asphalt pavement is heated. However, this device takes asphalt as a study object and can only obtain uniaxial shear strength. The Chinese patent CN104865137A and the Chinese patent CN105092387A respectively disclose a testing device for testing uniaxial tensile mechanical properties of a conductor material in a high temperature environment and an in-situ tensile testing system for high temperature mechanical properties of a small-sized monocrystalline silicon test piece, both of which are used to perform tensile mechanical testing. At present, some rock uniaxial mechanical experimental devices cannot be heated, or the heating temperature is very limited, so these devices cannot be used to test the mechanical parameters of rock under higher temperature, and basically do not have an acoustic speed testing function. Therefore, it is the top priority to use rock as a study object to directly perform a compression mechanical test to obtain the mechanical parameters such as uniaxial compressive strength, elastic modulus and Poisson's ratio of rock, which provide scientific analysis means and theoretical basis for high temperature rock mass geothermal development and oil and gas well engineering.

Technical Problems

The objective of the present invention is to provide a strain and acoustic wave testing device for a high temperature rock sample. This device may be used on a uniaxial mechanical tester to perform a strain and acoustic wave test experiment of rock under high temperature, record the temperature, axial strain and acoustic time difference of the rock sample during uniaxial compression in real time, and calculate mechanical parameters of rock, such as compressive strength, elastic modulus and Poisson's ratio, which provides a scientific analysis means for high temperature rock mass geothermal development and oil and gas well engineering.

Another objective of the present invention is to provide a method for performing a strain and acoustic wave test by using said device. The method is reliable in principle and easy to operate, the rock can be heated rapidly and efficiently to obtain the mechanical parameters of the rock under high temperature in real time, and the obtained experimental data are more accurate and reliable. Therefore, this method has a broad market application prospect.

SUMMARY

To fulfill said technical objectives, the present invention provides the following technical solutions.

A strain and acoustic wave testing device for a high temperature rock sample mainly comprises an upper pressure-bearing head, an acoustic wave transmitting terminal, an upper pressure-bearing shaft, corundum ejector pins, an upper displacement slide, an upper fixed foot block, a lower fixed foot block, a lower displacement slide, a heat insulation shell, a carbon fiber sleeve, a rock sample, a lower pressure-bearing shaft, a lower pressure-bearing head, an acoustic wave receiving terminal, a lower copper electrode, pearl powder, a temperature sensor, a transformer, a temperature-acoustic wave control box, an oscilloscope, an upper copper electrode, and a data collection and processing system.

The carbon fiber sleeve wraps the rock sample and is fixed inside the heat insulation shell through two pairs of upper and lower corundum ejector pins; a gap between the carbon fiber sleeve and the heat insulation shell is filled with perlite powder; the upper corundum ejector pins are used to fix the upper displacement slide through the upper fixed foot block, and the lower corundum ejector pins are used to fix the lower displacement slide through the lower fixed foot block; the upper displacement slide and the lower displacement slide are connected to the data collection and processing system respectively.

The upper end of the rock sample is connected to the acoustic wave transmitting terminal and the upper pressure-bearing head through the upper pressure-bearing shaft, and the lower end of the rock sample is connected to the acoustic wave receiving terminal and the lower pressure-bearing head through the lower pressure-bearing shaft; the upper copper electrode and the lower copper electrode are mounted on the upper pressure-bearing shaft and the lower pressure-bearing shaft respectively and are connected to the transformer respectively; the middle end of the rock ample is connected to the temperature sensor, the transformer and the temperature-acoustic wave control box; the temperature-acoustic wave control box is connected to the oscilloscope, the acoustic wave transmitting terminal and the acoustic wave receiving terminal respectively The carbon fiber sleeve, the temperature sensor, the oscilloscope and the temperature-acoustic wave control box are connected to the data collection and processing system respectively.

This device includes an intelligent heating portion, a rock sample axial strain testing portion, an acoustic wave testing portion, and a data collection and processing portion. The workflows of these four portions are briefly described below.

The intelligent heating portion: the transformer power is regulated by the temperature-acoustic wave control box, the transformer is connected to the upper and lower copper electrodes, and the upper and lower copper electrodes are also connected to the carbon fiber sleeve, so that the hot carbon fiber sleeve can be heated; the temperature sensor is also connected to the carbon fiber sleeve, and the temperature of the carbon fiber sleeve is fed back to the data collection and processing system; the data collection and processing system intelligently selects to stop heating or continue heating according to the fed-back temperature information to maintain the temperature at a specified temperature, for example, 500° C. The heating will be continued if the fed-back temperature is lower than 500° C., the heating is stopped if the temperature has reached 500° C., the heating will be performed again until 500° C. and then stopped if the temperature is gradually cooled to be lower than 500° C. after stopping heating. As such, the temperature is maintained at 500° C.

The rock sample axial strain testing portion: the upper displacement slide and the lower displacement slide are fixed on the two corundum ejector pins respectively by the upper and lower fixed foot blocks, and are connected to the data collection and processing system; the corundum ejector pins axially strain with the rock sample; the numerical value of the axial strain of the rock sample is equal to the displacement difference of the upper and lower displacement slides, and the displacement information is fed back to the data collection and processing system, and the specific values are displayed.

The acoustic wave testing portion: the temperature-acoustic wave control box is connected to the oscilloscope, the acoustic wave transmitting terminal and the acoustic wave receiving terminal respectively; the temperature-acoustic wave control box controls the acoustic wave transmitting terminal to emit acoustic waves, and the acoustic waves are received by the acoustic wave receiving terminal after being passing the rock sample; the measured acoustic wave data are displayed on the oscilloscope and stored in the data collection and processing system.

The data collection and processing portion: the measured heating data, rock sample axial strain data and acoustic wave data are displayed and stored in the data collection and processing system.

The method for performing a strain and acoustic wave test on a high temperature rock sample by using the above-mentioned device sequentially comprises the following steps:

(1) mounting the device on a uniaxial mechanical tester stroke;

(2) regulating the transformer by the temperature-acoustic wave control box to emit current, heating the carbon fiber sleeve and the rock sample in the carbon fiber sleeve through the upper copper electrode and the lower copper electrode, and maintaining the rock sample in the carbon fiber sleeve at a set temperature through the data collection and processing system;

(3) turning on a uniaxial mechanical tester to perform a compression test;

(4) acquiring a difference between the upper displacement slide and the lower displacement slide as an axial strain value of the rock sample in a high-temperature compression process since the corundum ejector pins move axially along with the rock sample in an axial strain process of the rock sample under compression;

(5) transmitting acoustic waves from the acoustic wave transmitting terminal by using the temperature-acoustic wave control box, receiving the acoustic waves by the acoustic wave receiving terminal after the waves pass through the rock sample, and displaying a waveform diagram of the rock sample during high-temperature uniaxial compression process in the oscilloscope to obtain an acoustic wave temporal difference of the rock sample in the high-temperature compression process; and (6) collecting various data and storing the data by the data collection and processing system, and calculating the mechanical parameters of rock, such as compressive strength, Poisson's ratio, and elastic modulus.

BENEFICIAL EFFECTS

Compared with the prior art, the present invention has the following beneficial effects:

(1) the device can not only test the uniaxial mechanical parameters of rock under high temperature, but also test the uniaxial mechanical parameters of a rock sample after high temperature cooling;

(2) the device has its own axial strain testing function, and thus can be used for performing an experiment instead of a jack in the case where a uniaxial mechanical tester is absent;

(3) the carbon fiber has good elasticity in thermal conductivity, the temperature of the rock sample can rise rapidly, and the carbon fiber deforms together with the wrapped rock sample, without affecting the experimental results of the lateral binding force of the rock sample;

(4) as a thermal insulation layer, the perlite powder can not only prevent the temperature of the carbon fiber sleeve from dissipating, but also prevent the temperature of a shell from being too high and burning an experimental operator;

(5) the tested acoustic data can be used to calculate other mechanical parameters of the rock.

BRIEF DESCRIPTION OF THE DRAWINGS

FIG. 1 is a schematic structural diagram of a strain and acoustic wave testing device of a high temperature rock sample.

In drawing, reference symbols represent the following components: 1—upper pressure-bearing head; 2—acoustic wave transmitting terminal; 3—upper pressure-bearing shaft; 4—corundum ejector pin; 5—upper displacement slide; 6—upper fixed foot block; 7—lower fixed foot block; 8—lower displacement slide; 9—heat insulation shell; 10—carbon fiber sleeve; 11—rock sample; 12—lower pressure-bearing shaft; 13—lower pressure-bearing head; 14—acoustic wave receiving terminal; 15—lower copper electrode; 16—pearl powder; 16—temperature sensor; 18—transformer; 19—temperature-acoustic wave control box; 20—oscilloscope; 21—upper copper electrode; 22—data collection and processing system.

DETAILED DESCRIPTION OF THE EMBODIMENTS

The present invention will be further described below in conjunction with the accompanying drawings.

Refer to FIG. 1.

A strain and acoustic wave testing device for a high temperature rock sample mainly comprises an upper pressure-bearing head 1, an acoustic wave transmitting terminal 2, an upper pressure-bearing shaft 3, corundum ejector pins 4, an upper displacement slide 5, an upper fixed foot block 6, a lower fixed foot block 7, a lower displacement slide 8, a heat insulation shell 9, a carbon fiber sleeve 10, a rock sample 11, a lower pressure-bearing shaft 12, a lower pressure-bearing head 13, an acoustic wave receiving terminal 14, a lower copper electrode 15, pearl powder 16, a temperature sensor 17, a transformer 18, a temperature-acoustic wave control box 19, an oscilloscope 20, an upper copper electrode 21, and a data collection and processing system 22.

The carbon fiber sleeve 10 wraps the rock sample 11 and is fixed inside the heat insulation shell 9 through two pairs of upper and lower corundum ejector pins 4; a gap between the carbon fiber sleeve and the heat insulation shell is filled with perlite powder 16; the upper corundum ejector pins are used to fix the upper displacement slide 5 through the upper fixed foot block 6, and the lower corundum ejector pins are used to fix the lower displacement slide 8 through the lower fixed foot block 7; the upper displacement slide and the lower displacement slide are connected to the data collection and processing system 22 respectively.

The upper end of the rock sample is connected to the acoustic wave transmitting terminal 2 and the upper pressure-bearing head 1 through the upper pressure-bearing shaft 3, and the lower end of the rock sample is connected to the acoustic wave receiving terminal 14 and the lower pressure-bearing head 13 through the lower pressure-bearing shaft 12; the upper copper electrode 21 and the lower copper electrode 15 are mounted on the upper pressure-bearing shaft and the lower pressure-bearing shaft respectively and are connected to the transformer 18 respectively; the middle end of the rock sample is connected to the temperature sensor 17, the transformer 18 and the temperature-acoustic wave control box 19; the temperature-acoustic wave control box is connected to the oscilloscope 20, the acoustic wave transmitting terminal 2 and the acoustic wave receiving terminal 14 respectively.

The carbon fiber sleeve 10, the temperature sensor 17, the oscilloscope 20 and the temperature-acoustic wave control box 19 is connected to the data collection and processing system 22 respectively.

A method for performing a strain and acoustic wave test by using the above-mentioned device sequentially comprises the following steps:

(1) mounting the device on a uniaxial mechanical tester stroke;

(2) regulating the transformer by the temperature-acoustic wave control box to emit current, heating the carbon fiber sleeve and further the rock sample in the carbon fiber sleeve through the upper copper electrode and the lower copper electrode, monitoring the temperature of the carbon fiber sleeve by the temperature sensor in real time, and maintaining the rock sample in the carbon fiber sleeve at a set temperature through the data collection and processing system, and keeping a constant temperature for a period of time after the rock sample reaches the set temperature, thereby ensuring that the rock sample is heated uniformly;

(3) turning on a uniaxial mechanical tester to perform a compression test;

(4) acquiring a difference between the upper displacement slide and the lower displacement slide as an axial strain value of the rock sample in a high-temperature compression process since the corundum ejector pins move axially along with the rock sample in an axial strain process of the rock sample under compression;

(5) transmitting acoustic waves from the acoustic wave transmitting terminal by using the temperature-acoustic wave control box, receiving the acoustic waves by the acoustic wave receiving terminal after the waves pass through the rock sample, and displaying a waveform diagram of the rock sample during high-temperature uniaxial compression process in the oscilloscope to obtain an acoustic wave temporal difference of the rock sample in the high-temperature compression process;

(6) storing various data in the data collection and processing system, and calculating the mechanical parameters of rock, such as compressive strength, Poisson's ratio, and elastic modulus; and (7) at the end of the experiment, a power source is turned off, and after the device is cooled to room temperature, the rock sample is replaced for the next round of experiments.

What is claimed is:

1. A strain and acoustic wave testing device for a high temperature rock sample, comprising: an upper pressure-bearing head, an acoustic wave transmitting terminal, an upper pressure-bearing shaft, corundum ejector pins, an upper displacement slide, an upper fixed foot block, a lower fixed foot block, a lower displacement slide, a heat insulation shell, a carbon fiber sleeve, a rock sample, a lower pressure-bearing shaft, a lower pressure-bearing head, an acoustic wave receiving terminal, a lower copper electrode, pearl powder, a temperature sensor, a transformer, a temperature-acoustic wave control box, an oscilloscope, an upper copper electrode, and a data collection and processing system, wherein the carbon fiber sleeve wraps the rock sample and is fixed inside the heat insulation shell through two pairs of upper and lower corundum ejector pins;

a gap between the carbon fiber sleeve and the heat insulation shell is filled with perlite powder;

the upper corundum ejector pins are used to fix the upper displacement slide through the upper fixed foot block, and the lower corundum ejector pins are used to fix the lower displacement slide through the lower fixed foot block;

the upper displacement slide and the lower displacement slide are connected to the data collection and processing system respectively;

an upper end of the rock sample is connected to the acoustic wave transmitting terminal and the upper pressure-bearing head through the upper pressure-bearing shaft, and a lower end of the rock sample is connected to the acoustic wave receiving terminal and the lower pressure-bearing head through the lower pressure-bearing shaft;

the upper copper electrode and the lower copper electrode are mounted on the upper pressure-bearing shaft and the lower pressure-bearing shaft respectively and are connected to the transformer respectively;

a middle end of the rock sample is connected to the temperature sensor, the transformer and the temperature-acoustic wave control box;

the temperature-acoustic wave control box is connected to the oscilloscope, the acoustic wave transmitting terminal and the acoustic wave receiving terminal respectively; and the carbon fiber sleeve, the temperature sensor, the oscilloscope and the temperature-acoustic wave control box are connected to the data collection and processing system respectively.

* * * * *